(12) United States Patent
McDonald

(10) Patent No.: US 8,979,530 B2
(45) Date of Patent: Mar. 17, 2015

(54) REUSABLE DENTAL IMPRESSION TRAY

(75) Inventor: Simon Paul McDonald, Katikati (NZ)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/876,818

(22) PCT Filed: Sep. 29, 2011

(86) PCT No.: PCT/US2011/054089
§ 371 (c)(1), (2), (4) Date: May 17, 2013

(87) PCT Pub. No.: WO2012/047731
PCT Pub. Date: Apr. 12, 2012

(65) Prior Publication Data
US 2013/0224680 A1  Aug. 29, 2013

(30) Foreign Application Priority Data

Sep. 29, 2010 (NZ) ........................................ 588307
May 6, 2011 (NZ) ........................................ 592695

(51) Int. Cl.
*A61C 9/00* (2006.01)
(52) U.S. Cl.
CPC .................................. *A61C 9/0006* (2013.01)
USPC ...................................................... 433/37
(58) Field of Classification Search
CPC .................................................... A61C 9/0006
USPC ............ 433/6, 34, 37–48, 214; 128/861, 862
See application file for complete search history.

(56) References Cited

U.S. PATENT DOCUMENTS

| 3,468,029 | A |   | 9/1969 | Moore |       |
|-----------|---|---|--------|-------|-------|
| 4,204,323 | A | * | 5/1980 | Neubert et al. | 433/38 |

(Continued)

FOREIGN PATENT DOCUMENTS

| DE | 20319430 U1 | 4/2004 |
| FR | 2250507 A1 | 6/1975 |
| WO | 2007132168 A1 | 11/2007 |

OTHER PUBLICATIONS

European Patent Office Acting as the International Search Authority, "International Preliminary Report on Patentability (Chapter I of the Patent Cooperation Treaty)," PCT/US2011/054089, Apr. 11, 2013.

(Continued)

*Primary Examiner* — Eric Rosen
(74) *Attorney, Agent, or Firm* — IpHorgan Ltd.

(57) ABSTRACT

A reusable dental impression tray having a reusable rigid tray holder with opposing sidewalls spaced apart substantially a first distance, a connector at a distal end of the tray holder couples the sidewalls together, the sidewalls and connector define an inward facing surface, a channel formed in and extends along the inward facing surface, and a disposable mesh bite tray having a generally U-shaped frame having an open end and a closed end, the U-shaped frame is made of a flexible material wherein the U-shaped frame has a static shape having a width at the closed end substantially the first distance and a width at the open end which is greater than the first distance, wherein with the U-shaped frame received in the channel, the open and of the U-shaped frame is held with the open end having a compressed width substantially the same as the first distance.

14 Claims, 7 Drawing Sheets

(56) References Cited

U.S. PATENT DOCUMENTS

| | | | |
|---|---|---|---|
| 4,763,791 A * | 8/1988 | Halverson et al. | 206/570 |
| 5,820,372 A | 10/1998 | Jones | |
| 2006/0068357 A1 * | 3/2006 | Paradiso et al. | 433/39 |
| 2006/0088799 A1 | 4/2006 | Dorfman et al. | |
| 2006/0808799 | 4/2006 | Dorfman et al. | |
| 2008/0044797 A1 * | 2/2008 | Bardach et al. | 433/217.1 |
| 2010/0227289 A1 * | 9/2010 | Farrell | 433/6 |

OTHER PUBLICATIONS

European Patent Office Acting as the International Search Authority, International Search Report, PCT/US2011/054089, Apr. 12, 2012.

European Patent Office Acting as the International Search Authority, International Preliminary Report on Patentability (Chapter I of the Patent Cooperation Treaty), PCT/US2011/054089, Apr. 11, 2013.

* cited by examiner

REUSABLE DENTAL IMPRESSION TRAY

CROSS-REFERENCE TO RELATED APPLICATIONS

This application claims the priority to New Zealand Application No. 588307, filed Sep. 29, 2010, and New Zealand Application No. 592695, filed May 6, 2011, the entire contents of which both are hereby incorporated by reference.

FIELD OF THE INVENTION

The present invention relates to a dental impression tray, and in particular, a reusable dental impression tray for taking an impression of the posterior teeth.

BACKGROUND OF THE INVENTION

The prior art includes dental impression trays designed for taking an impression of all or some of the lower or upper teeth. Such trays are often a single piece device made of all metal or other material which is autoclavable. The prior art also includes dental instruments for taking posterior impressions. Such dental impression trays may be extremely rigid and reusable. Dental impression trays are anatomically shaped to fit over the patient's teeth. An impression material is then secured in the tray, often with an adhesive, before being placed inside the patient's mouth where they bite down on the impression material until it sets. The tray, with set impression material, is then removed from the patient's mouth and is used as a mould to form a model of the patient's dentition.

U.S. Pat. No. 3,468,029 discloses a dental impression frame and disposable tray. The frame is split and hinged at one end so the frame may clamp down on a gauge material, firmly, on all but one side, such as the lingual, wherein the gauge material is secured but to allow slippage as the gauge material is pulled while being clamped between the teeth. U.S. Pat. No. 5,820,372 discloses a dental impression tray. The tray includes a frame and handle member and removable impression tray.

In order to make accurate and quality impressions, moulds and dental prostheses, the stability of the bite tray is critical. Current bite trays lack this stability due to their construction material and/or design.

SUMMARY OF THE INVENTION

It is an object of the present invention to provide a rigid dental impression tray that overcomes the problems of the prior art dental impression trays and produces an accurate, undistorted impression.

It is a further object of the present invention to include a secure method of attaching the impression material to the dental impression tray.

It is still a further object of the present invention to offer a dental impression tray that fits almost any mouth shape.

It is yet a further object of the present invention to provide a dental impression tray which does not require the use of an adhesive.

It is still yet a further object of the present invention to provide a cost effective dental impression tray.

The present invention therefore provides a reusable dental impression tray having a reusable rigid tray holder with opposing sidewalls spaced apart substantially a first distance, the opposing sidewalls extend longitudinally in a curved manner, a connector located at a distal end of the tray holder couples the sidewalls together, the sidewalls and connector define an inward facing surface, a channel formed in and extends along the inward facing surface, and a handle located at a mesial end of the tray holder, and a disposable mesh bite tray having a generally U-shaped frame having an open end and a closed end, the U-shaped frame is made of a flexible material wherein the U-shaped frame has a generally static shape having a width at the closed end substantially similar to the first distance and a width at the open end which is greater than the first distance, and wherein with the U-shaped frame received in the channel, the open end of the U-shaped frame is held in a compressed state with the open end having a compressed width substantially the same as the first distance.

The present invention further provides a corresponding kit, as well as a corresponding disposable mesh bite tray.

DETAILED DESCRIPTION OF THE INVENTION

Figure 1:
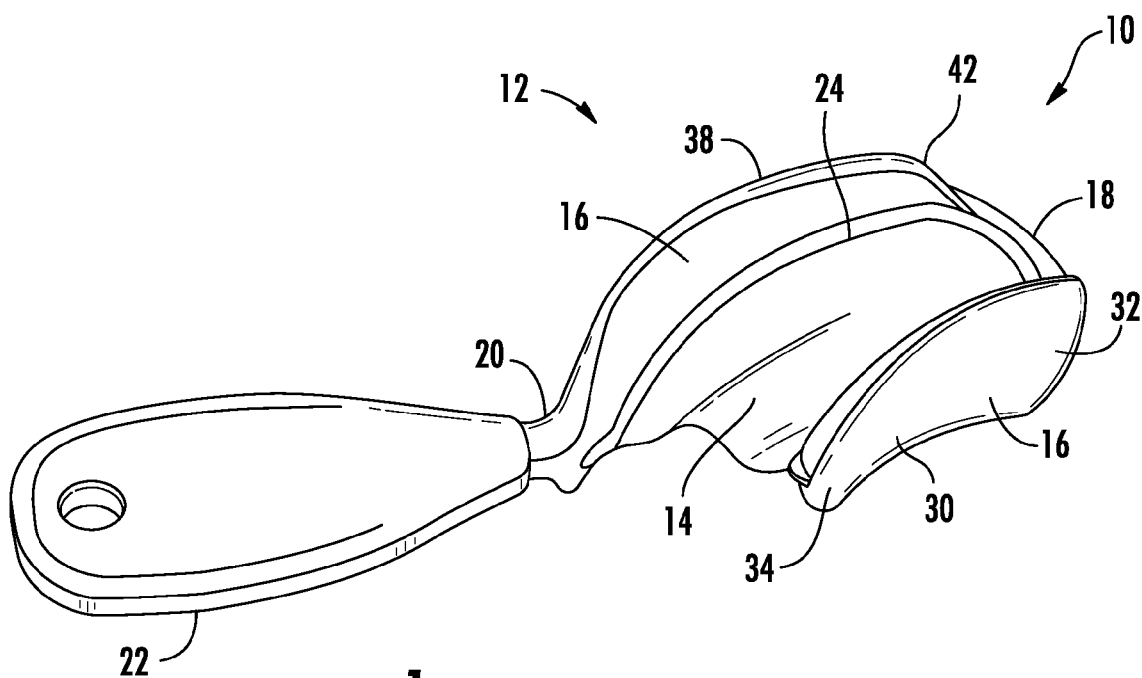
FIG. 1 is a perspective view of a reusable dental impression tray in accordance with one embodiment of the present invention, including the reusable tray holder and the disposable biting tray.

FIG. 1 shows a reusable dental impression tray 10 in accordance with one embodiment of the present invention. The reusable dental impression tray 10 includes a reusable tray holder 12 and a disposable bite tray 14. The reusable tray holder 12 includes a pair of opposing sidewalls or fins 16 connected via a curved arm or connector 18. The reusable tray holder 12 further includes a stem 20 upon which a handle 22 is secured thereto. Alternatively, the reusable tray holder 12 may be a one-piece component, including the handle. The handle includes a smooth surface. The smooth surface facilitates writing or attaching tracking details. In addition, the handle or some other part of the reusable tray holder 12 may be color coded to represent difference sizes of the reusable tray holder 12. The slim design fits comfortably in the patient's mouth. The opposing sidewalls are anatomically designed to support impression material evenly. The solid walls of the opposing sidewalls impose a hydraulic pressure on the impression material.

The curved connector 18 is reinforced to prevent the dental impression tray 10 from twisting. The curved connector 18 may be approximately 2 mm to 3 mm high and 3-6 mm wide. In one embodiment, the connector 18 is approximately 4 mm wide.

Figure 2:
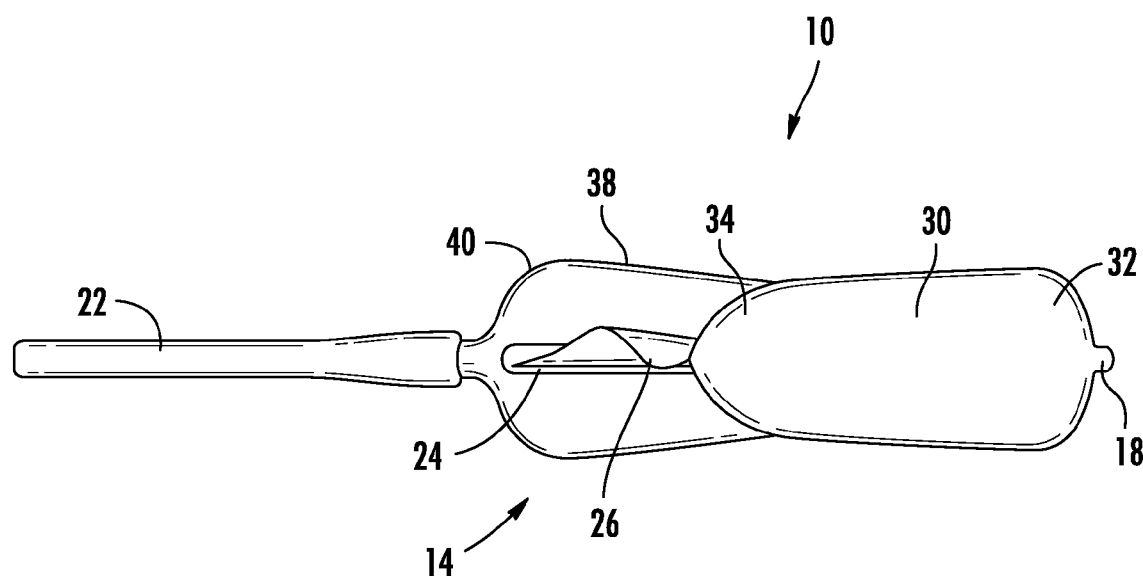
FIG. 2 is a back side view of the reusable dental impression tray of FIG. 1 in accordance with the present invention.

FIG. 2 shows a back side view of the reusable dental impression tray 10. It can be seen that the disposable bite tray 14 includes a frame 24 and a mesh 26. It is apparent from FIG. 2 that the mesh is not taut. Rather, the mesh 26 forms a wave or ripple. FIG. 2 also shows that the lingual or palatal sidewall 30 includes a distal end 32 having a curved and blunt profile. The lingual sidewall 30 further includes a mesial end 34 having a curved and more pointed profile. It will be noted that the lingual sidewall 30 tapers from a wide distal end 32 to the narrower mesial end 34. The lingual sidewall 30 is designed to control the tongue so as to prevent distorted impressions. In addition, the mesial end 34 of the lingual sidewall 30 provides the smaller or pointed profile in part for shallow palates.

FIGS. 1 and 2 also show that the buccal sidewall 38 includes a mesial end 40 having a curved and blunt profile. The buccal sidewall 38 further includes a distal end 42 having a curved and more pointed profile. It will be noted that the buccal sidewall 38 tapers from a wide mesial end 40 to a narrower distal end 42. The frame 24 may be color coded to represent difference sizes of the disposable bite tray 14, in the same manner as the handle.

Figure 3:
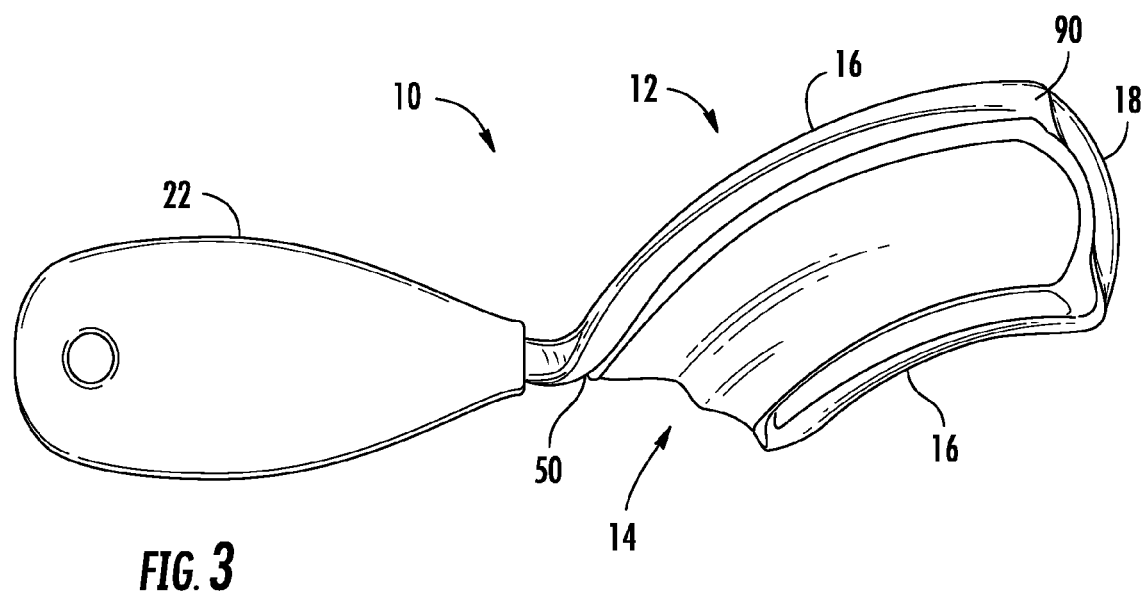
FIG. 3 is a top view of the reusable dental impression tray of FIG. 1 in accordance with the present invention.
Figure 4:
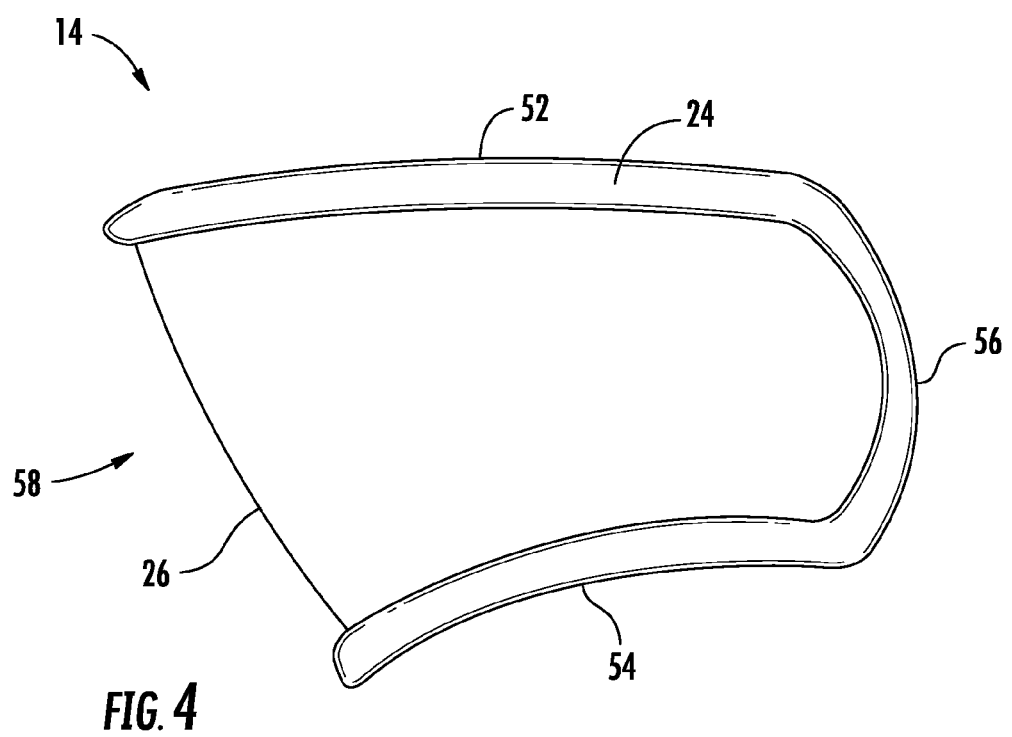
FIG. 4 is a top view of the disposable biting tray of FIG. 1 in accordance with the present invention.
Figure 5:
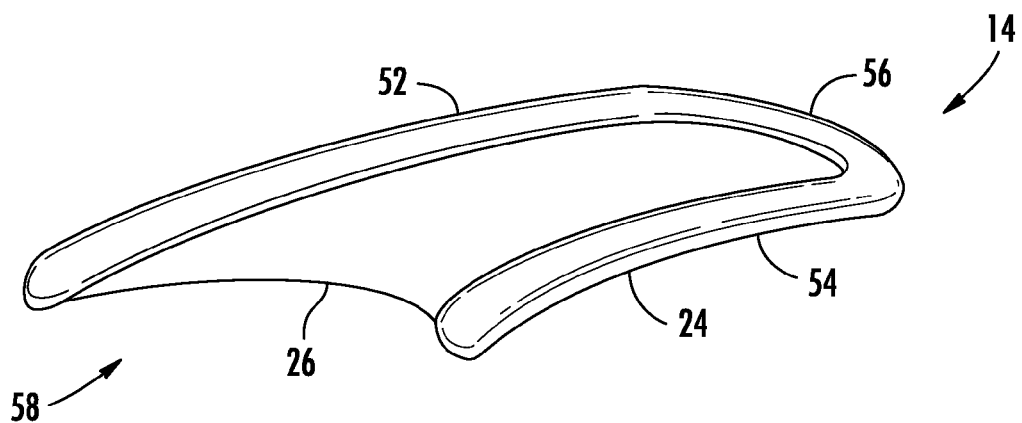
FIG. 5 is a perspective view the disposable biting tray of FIG. 1 in accordance with the present invention.

FIG. 3 shows a top view of the reusable dental impression tray 10. The opposing sidewalls 16 are readily apparent to be arched so as to conform with the posterior teeth. The disposable bite tray 14 is shown extending between the opposing sidewalls 16 within a groove or channel 50. FIG. 4 shows the disposable bite tray 14 having the molded springy frame 24 and the mesh 26. FIG. 5 is a perspective view of the disposable bite tray 14. The molded springy frame 24 includes a buccal portion 52, a lingual portion 54, a connector 56, and an open end 58. FIG. 4 shows that the distance between the buccal portion 52 and lingual portion 54 is wider at the open end 58 in comparison to the connector portion 56. This is the static state or position of the disposable bite tray 14, with the buccal portion 52 and lingual portion 54 diverging from the connector portion 56.

Figure 6:
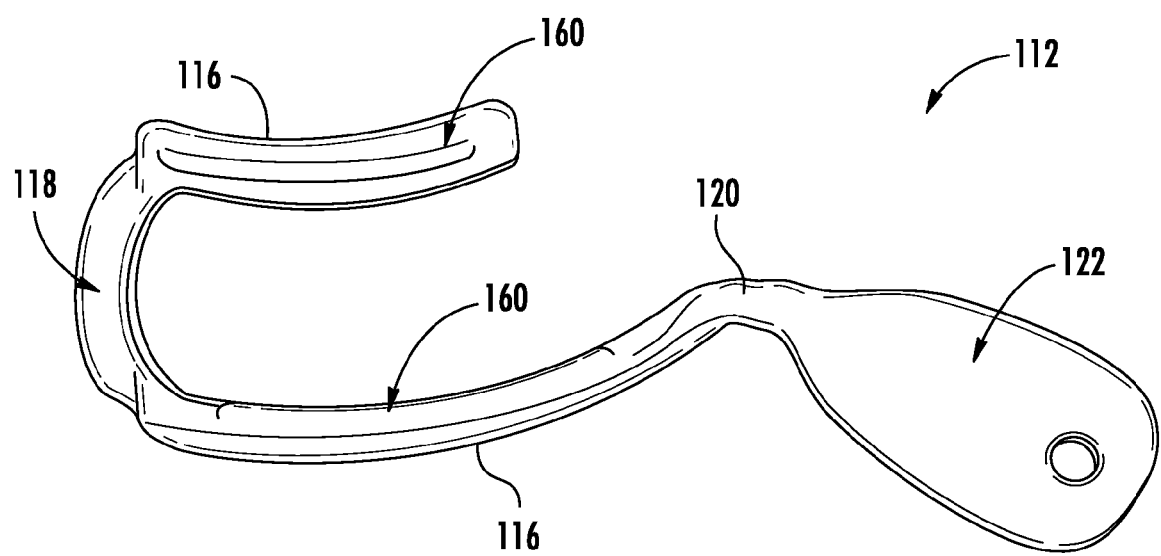
FIG. 6 is a top view of a reusable tray holder in accordance with a second embodiment of the present invention.
Figure 7:
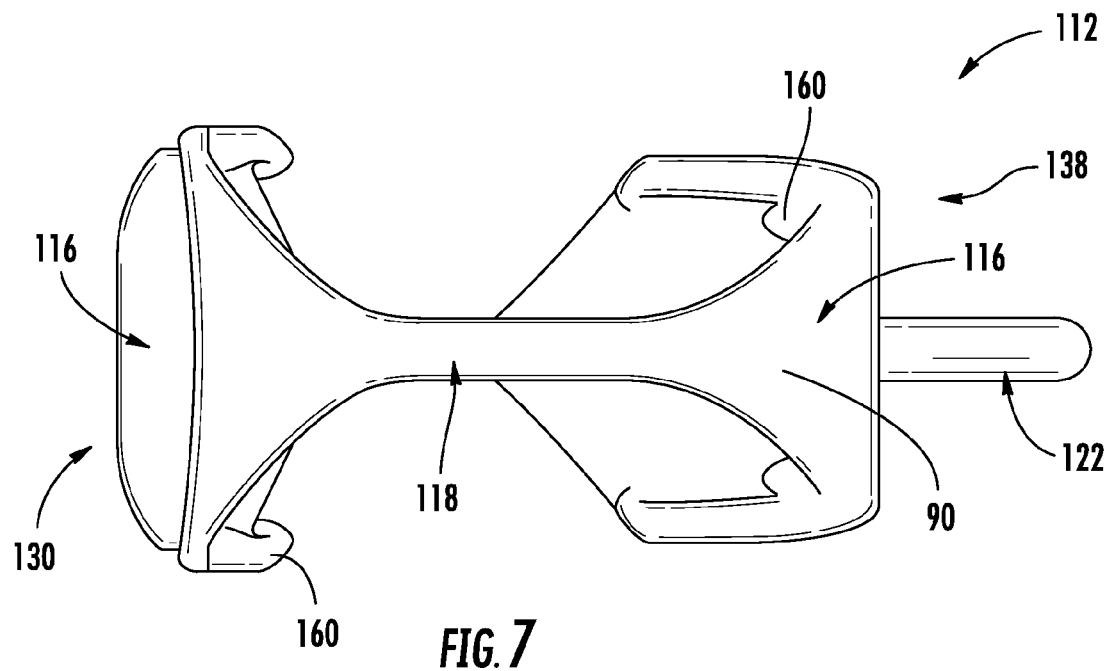
FIG. 7 is an end view of the reusable tray holder of FIG. 6 in accordance with the present invention.
Figure 8:
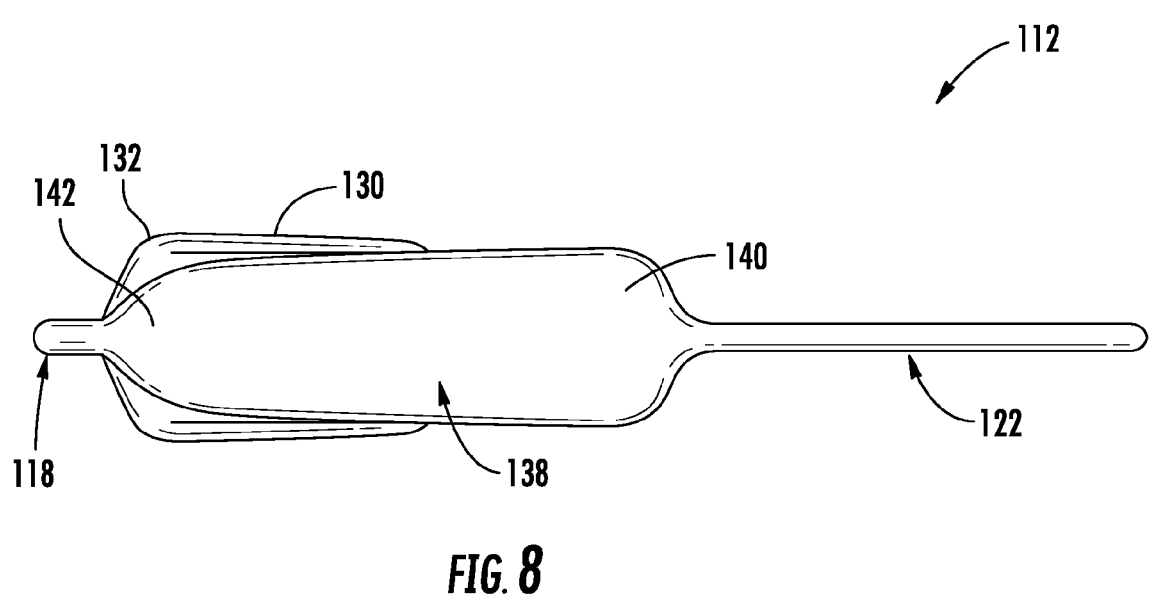
FIG. 8 is a back side view of the reusable tray holder of FIG. 6 in accordance with the present invention.

FIG. 6 shows a top view of a reusable tray holder 112 in accordance with a second embodiment. The reusable tray holder 112 includes opposing sidewalls or fins 116 connected via a connector 118. A handle 122 is coupled to the reusable tray holder 112 via a stem 120. The opposing sidewalls 116 include a pair of ledges 160. FIG. 7 shows a back side view of the reusable tray holder 112 wherein the ledges 160 are seen on the lingual sidewall 130 and the buccal sidewall 138. FIG. 8 shows a back side view of the reusable tray holder 112, wherein the buccal sidewall 138 includes a mesial end 140 having a curved and blunt profile. The buccal sidewall 138 further includes a distal end 142 having a curved and more pointed profile. It will be noted that the buccal sidewall 138 tapers from a wide mesial end 140 to a narrower distal end 142. The narrower distal end 142 of the buccal sidewall 138 prevents impingment on tissues. In contrast, the wider or taller mesial end 140 of the buccal wall 138 supports the canine teeth.

Figure 11:
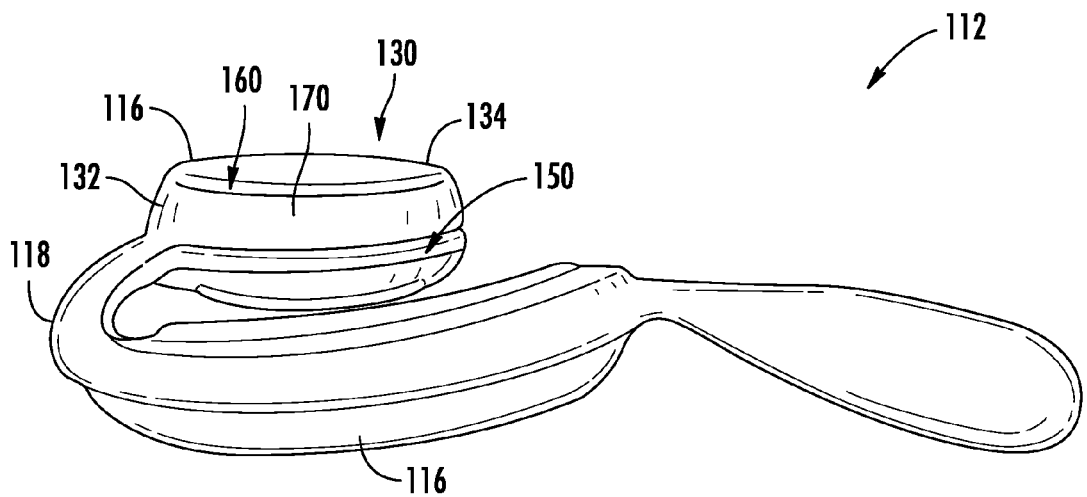
FIG. 11 is a perspective front view of the reusable tray holder of FIG. 6 in accordance with the present invention.

As can be seen from FIGS. 8 and 11, the lingual or palatal sidewall 130 includes a distal end 132 having a curved and blunt profile. The lingual sidewall 130 further includes a mesial end 134 having a curved and more pointed profile. It will be noted that the lingual sidewall 130 tapers from a wide distal end 132 to a narrower mesial end 134.

Figure 9:
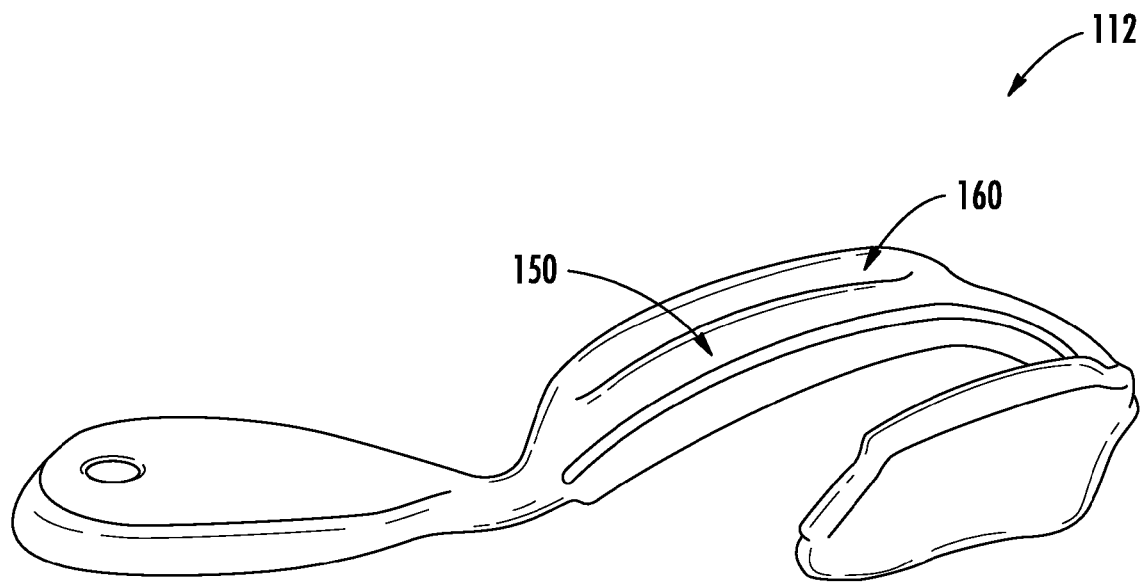
FIG. 9 is a perspective view of the span between the opposing sidewalls of the reusable tray holder of FIG. 6 in accordance with the present invention.
Figure 10:
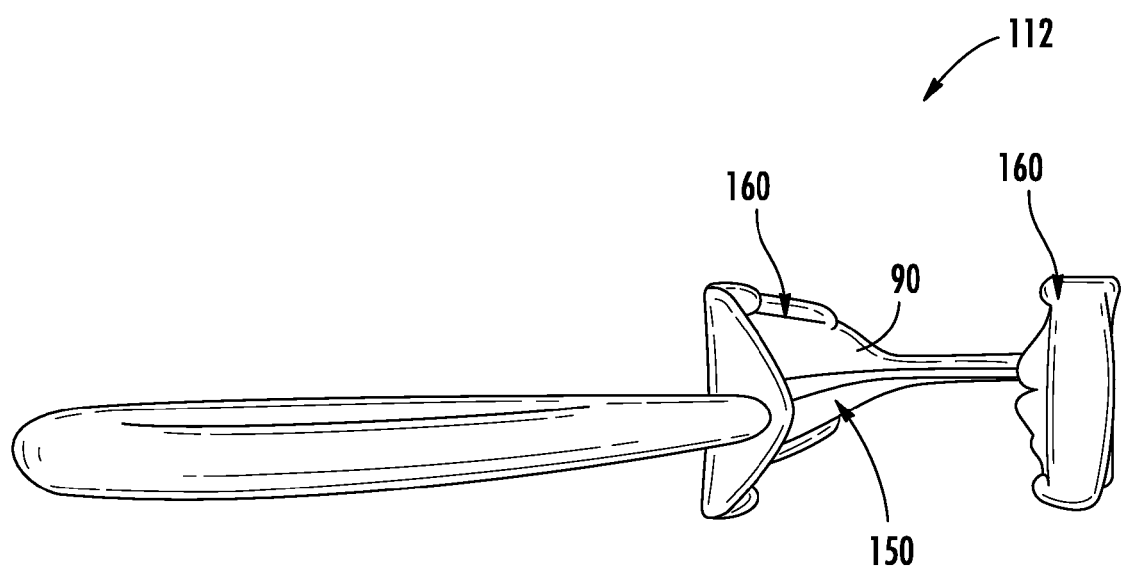
FIG. 10 is an end view of the span between the opposing sidewalls of the reusable tray holder of FIG. 6 in accordance with the present invention.

FIGS. 9-11 show the reusable holder 112 of the second embodiment, wherein a groove or channel 150 extends along the middle of the inwardly facing surface 170 of the opposing sidewalls 116 and connector 118.

Figure 12:
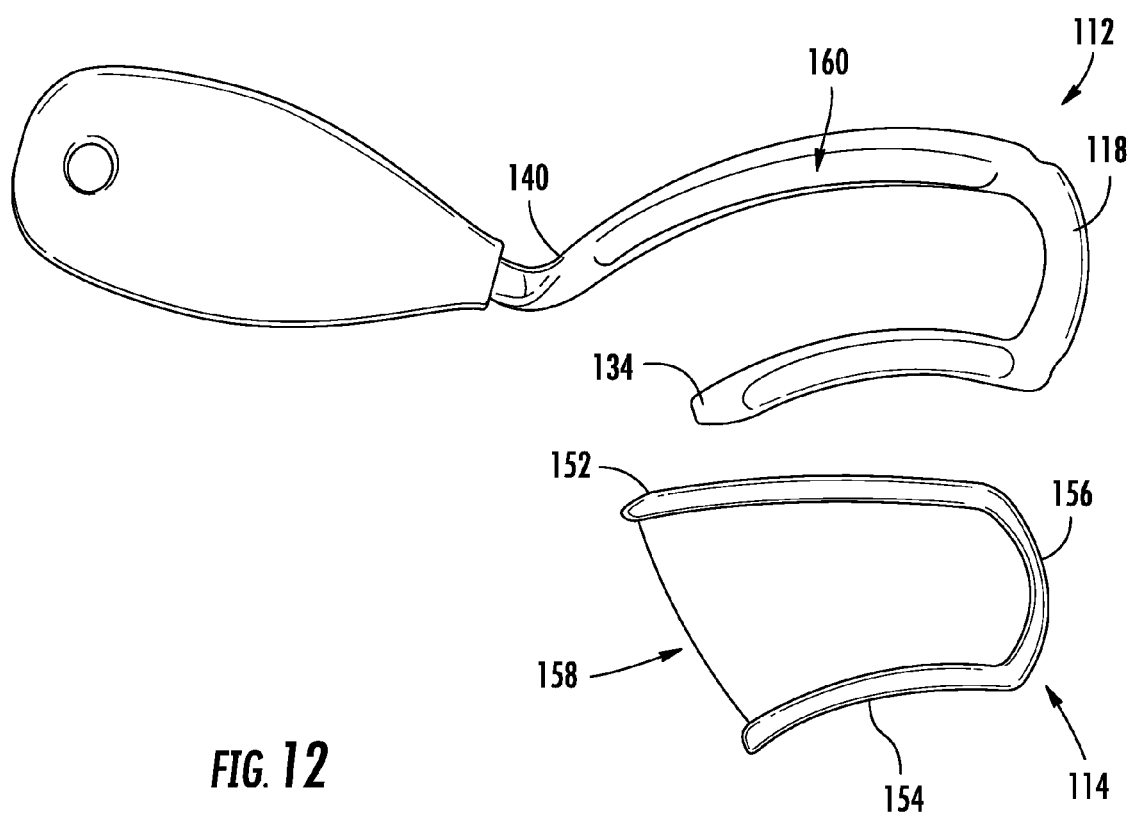
FIG. 12 is a side-by-side top view of the reusable tray holder and disposable mesh insert tray of FIG. 6 in accordance with the present invention.

FIG. 12 shows the side-by-side comparison of the reusable tray holder 112 and the disposable bite tray 114. It can be seen that the connector portion 156 substantially conforms to the dimensions of the groove or channel 150 at the connector 118. However, the open end 158 as defined by at the buccal portion 152 and lingual portion 154 is wider than the holder open end defined at the mesial end 134 and mesial end 140. It will be appreciated that with the disposable bite tray 114 is inserted into the channel 150 towards the connector 118, the buccal portion 152 and lingual portion 154 and urged together with increasing tension as the open end 158 approaches the channel 150. With the disposable bite tray 114 fully inserted into the reusable tray holder 112, buccal portion 152 and lingual portion 154 maintain a constant outward tension so as to create a compression fit within the channel 150 and remain securely in place throughout the impression and mold process steps. The dimensions of the channel and frame may be selected to additionally provide an interference fit, for greater securement.

FIGS. 3, 7 and 10, in particular, show the flared nature of the opposing sidewalls. The flared opposing sidewalls self-lock impression material against displacement forces. FIGS. 1, 3, 7 and 10, in particular, show how the curved intersection of the connector and sidewalls define a back seal 90 which prevents distal overflow of the impression material. The self-locking nature of the reusable tray holder means that an adhesive is not required, but is optional.

Figure 13:
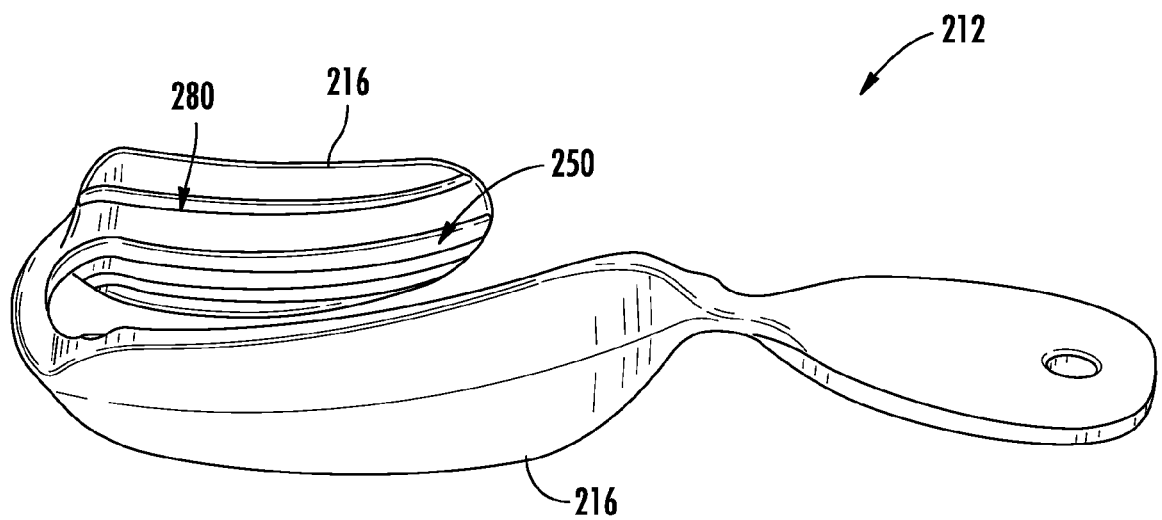
FIG. 13 is a front perspective view of the reusable tray holder in accordance with a third embodiment of the present invention.
Figure 14:
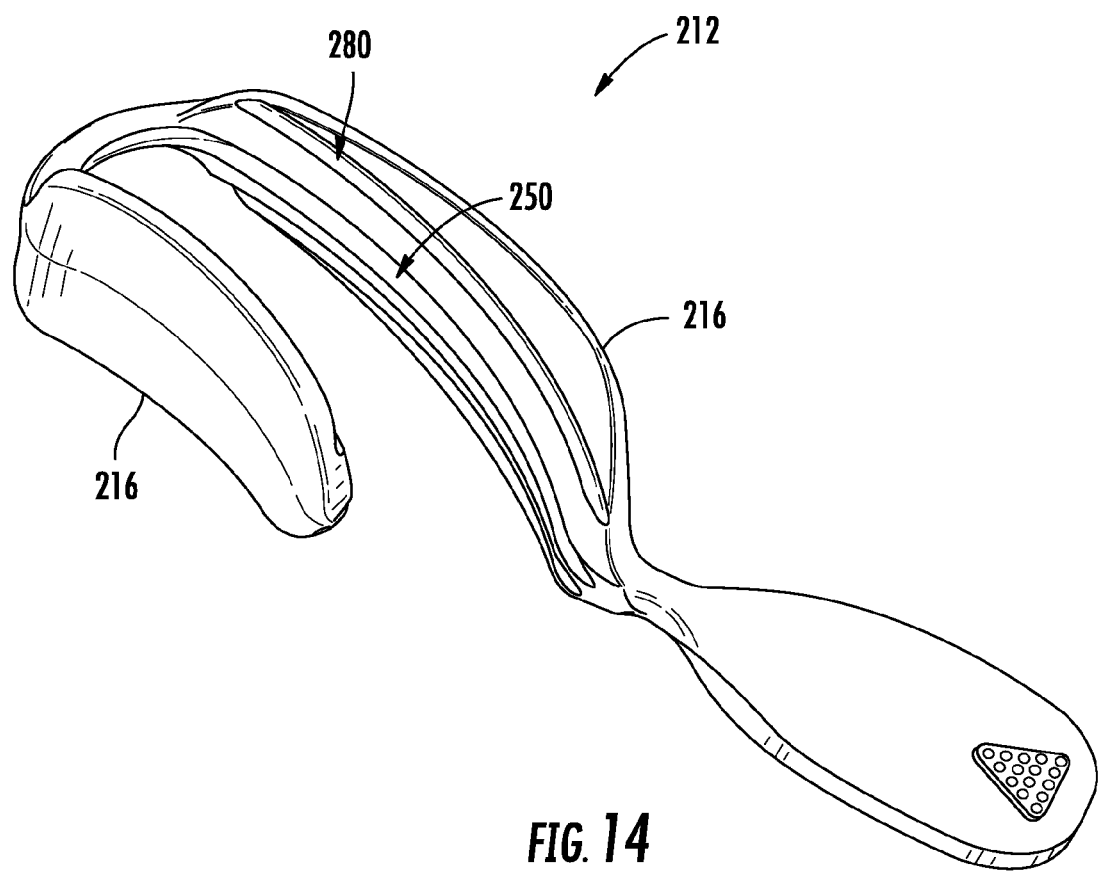
FIG. 14 is a front perspective view of the reusable tray holder in accordance with the third embodiment of the present invention.

FIG. 13 shows a front perspective view of the reusable tray holder 212 in accordance with a third embodiment of the invention. Instead of ledges 160, the top and bottom of the opposing sidewalls or fins 216 are provided with slots 280. The slots 280 may extend horizontally, as shown, or at any other angle. For example, the slots may extend parallel to one another but angularly with respect to the channel. Still further, the slots may diverge from one another, in a distal direction. It will be understood that other orientations of the slots are possible as well. The slots 280 allow the impression material to flow through the slots 280. Once the impression material sets, the impression material is held firmly in place.

The reusable tray holder may be made of a rigid material such as stainless steel or titanium. FIG. 13 is an example of a one-piece reusable tray holder. A color coded label or indicia is provided on the handle to identify the size of the reusable tray holder.

In practice, the appropriate sized reusable rigid tray holder is selected based on the color code and the particular patient. A corresponding disposable bite tray is similarly selected based on the same color code. The disposable bite tray is fitted to the reusable tray holder and is then loaded with the impression material which adheres to the tray holder and bite tray without the use of an adhesive. The reusable dental impression tray with impression material is placed inside the patient's mouth and the patient bites down on the soft impression material until the material sets. The tray and impression material is then removed from the patient's mouth and sent to the dental laboratory. Dental stone is poured into the impression to form a model of the patient's tooth dentition. Due to the rigidity of the tray holder, multiple impressions can then be cast without the impression material deforming. Once all casting is complete, the disposable bite tray is removed from the reusable rigid tray holder, along with the impression material. The reusable rigid tray holder can then be cleaned and sterilized, and a new disposable bite tray may be inserted, ready for use.

While the present invention has been described in connection with a specific application, this application is exemplary in nature and is not intended to be limiting on the possible applications of this invention. It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

I claim:

1. A reusable dental impression tray comprising: a reusable rigid tray holder with opposing sidewalls spaced apart substantially a first distance, the opposing sidewalls extend longitudinally in a curved manner, one of the opposing sidewalls defines a buccal sidewall and the other opposing sidewall defines a lingual or palatal sidewall, a connector located at a distal end of the tray holder couples the sidewalls together, the sidewalls and connector define an inward facing surface, a channel portion in the buccal sidewall, a channel portion in the lingual or palatal sidewall, a channel portion in the connector located at the distal end, where the channel portions in the buccal sidewall, lingual or palatal sidewall, and the connector located at the distal end form a continuous generally U-shaped channel in the inward facing surface, the channel portion in the buccal sidewall and the channel portion of the lingual or palatal sidewall are spaced apart substantially a second distance, and a handle located at a mesial end of the tray holder; and a disposable mesh bite tray having a generally U-shaped frame having an open end and a closed end, the U-shaped frame is made of a flexible material wherein the U-shaped frame has a static shape having a width at the closed end substantially the second distance and a width at the open end a third distance which is greater than the second distance, and wherein with the U-shaped frame received in the U-shaped channel, the open end of the U-shaped frame is urged to a compressed state with the open end having a compressed width substantially the same as the second distance.

2. The reusable dental impression tray of claim 1 wherein the distal connector is approximately 2 mm to 3 mm high and 3-6 mm wide.

3. The reusable dental impression tray of claim 1 wherein the buccal sidewall includes a mesial end having a curved and blunt profile and a distal end having a curved and pointed profile, wherein a profile of the buccal sidewall tapers from a wide mesial end to a narrow distal end, and the lingual or palatal sidewall includes a distal end having a curved and blunt profile and a mesial end having a curved and pointed profile, wherein a profile of the lingual or palatal sidewall tapers from a wide distal end to a narrow mesial end.

4. The reusable dental impression tray of claim 1, wherein the inward facing surfaces of the opposing sidewalls are flared, the inward facing surface of the buccal sidewall extends from the U-shaped channel in a coronal and apical direction in a concave manner, and the inward facing surface of the lingual or palatal sidewall extends from the channel in a coronal and apical direction in a convex manner.

5. The reusable dental impression tray of claim 1, wherein the reusable rigid tray holder is made of a material selected from the group of stainless steel and titanium, and the opposing sidewalls present a solid and rigid structure.

6. The reusable dental impression tray of claim 1, wherein the reusable dental impression tray is color coded to identify the size of the tray.

7. The reusable dental impression tray of claim 1, wherein the handle includes a smooth surface for adding tracking information, and the handle extends from the opposing sidewalls at an angle in a direction which is substantially forward from a patient's mouth when in use.

8. The reusable dental impression tray of claim 1, further comprising a back seal formed by a curved intersection of the connector and sidewalks.

9. The reusable dental impression tray of claim 1, wherein the frame is received by the U-shaped channel in an interference fit.

10. The reusable dental impression tray of claim 1, further comprising inwardly curved ledges extending along the inward facing surface of the opposing sidewalls, spaced above and below the U-shaped channel.

11. The reusable dental impression tray of claim 1, further comprising slots extending along the inward facing surface of the opposing sidewalls, spaced above and below the U-shaped channel, wherein the slots extend parallel to the U-shaped channel or at an angle to the channel.

12. The reusable dental impression tray of claim 1, wherein the reusable rigid tray holder is a one-piece component, including the handle.

13. The reusable dental impression tray of claim 1, wherein the handle is made of plastic.

14. A kit for making dental impression, the kit comprising:
a first reusable rigid tray holder of a first size and a second reusable rigid tray holder of a second size,
both of the reusable rigid tray holders having opposing sidewalls spaced apart substantially a first distance, the opposing sidewalls extend longitudinally in a curved manner, one of the opposing sidewalls defines a buccal sidewall and the other opposing sidewall defines a lingual or palatal sidewall, a connector located at a distal end of the tray holder couples the sidewalls together, the sidewalls and connector define an inward facing surface, a channel portion in the buccal sidewall, a channel portion in the lingual or palatal sidewall, a channel portion in the connector located at the distal end, where the channel portions in the buccal sidewall, lingual or palatal sidewall, and the connector located at the distal end form a continuous generally U-shaped channel in the inward facing surface, the channel portion in the buccal sidewall and the channel portion of the lingual or palatal sidewall are spaced apart substantially a second distance, and a handle located at a mesial end of the tray holders;
and a plurality of a first disposable mesh bite tray of a first size corresponding to the size of the first reusable rigid tray holder, and a plurality of a second disposable mesh bite tray of a second size corresponding to the size of the second reusable rigid tray holder,
each disposable mesh bite tray having a generally U-shaped frame having an open end and a closed end, the U-shaped frame is made of a flexible material wherein the U-shaped frame has a static shape having a width at the closed end substantially the second distance respective rigid tray holder and a width at the open end a third distance which is greater than the second distance respective rigid tray holder, and wherein with the U-shaped frame received in the U-shaped channel respective rigid tray holder, the open end of the U-shaped frame is urged to a compressed state with the open end having a compressed width substantially the same as the second distance respective rigid tray holder.

\* \* \* \* \*